United States Patent [19]

Burtis et al.

[11] Patent Number: 4,740,472

[45] Date of Patent: Apr. 26, 1988

[54] METHOD AND APPARATUS FOR AUTOMATED PROCESSING AND ALIQUOTING OF WHOLE BLOOD SAMPLES FOR ANALYSIS IN A CENTRIFUGAL FAST ANALYZER

[75] Inventors: Carl A. Burtis, Oak Ridge; Wayne F. Johnson, Loudon; William A. Walker, Knoxville, all of Tenn.

[73] Assignee: The United States of America as represented by the United States Department of Energy, Washington, D.C.

[21] Appl. No.: 762,368

[22] Filed: Aug. 5, 1985

[51] Int. Cl.⁴ .................. B04B 5/02; B04B 11/00; B01D 21/26

[52] U.S. Cl. ........................ 436/63; 436/45; 436/177; 422/72; 210/512.1; 210/787; 494/16; 494/17

[58] Field of Search ............. 436/45, 63, 177; 422/72, 101; 210/512.1, 512.3, 787; 494/16, 17, 22

[56] References Cited

U.S. PATENT DOCUMENTS

| | | |
|---|---|---|
| 3,268,160 | 8/1966 | Talley ................... 494/16 |
| 3,555,284 | 1/1971 | Anderson . |
| 3,798,459 | 3/1974 | Anderson et al. . |
| 3,854,508 | 12/1974 | Burtis et al. . |
| 3,864,089 | 2/1975 | Tiffany et al. . |
| 3,890,101 | 6/1975 | Tiffany et al. . |
| 3,891,140 | 6/1975 | Ayres ................. 494/16 X |
| 3,899,296 | 8/1975 | Mailen et al. ......... 494/17 X |
| 4,052,164 | 10/1977 | König ................. 494/16 X |
| 4,169,060 | 9/1979 | Columbus ............. 494/16 X |

OTHER PUBLICATIONS

Burtis et al., "The Development of Rotors Having Separate Sample and Reagent Transfer Channels for Use with Centrifugal Fast Analyzers", Analytical Letters, 7(8&9), 1974.

J. C. Mailen et al., "Techniques for Fabrication and Assembly of Rotors for Use in a Miniature Fast Analyzer", Analytical Letters, 6(3), 1973.

C. A. Burtis et al., "Optimization and Analytical Applications of the Technique of Dynamic Introduction of Liquids into Centrifugal Analyzers", Advanced Concepts, Clin. Chem., 20/8, 1974.

Primary Examiner—Barry S. Richman
Assistant Examiner—Lynn M. Kummert
Attorney, Agent, or Firm—Stephen D. Hamel; Judson R. Hightower

[57] ABSTRACT

A rotor and disc assembly for use in a centrifugal fast analyzer. The assembly is designed to process multiple samples of whole blood followed by aliquoting of the resultant serum into precisely measured samples for subsequent chemical analysis. The assembly requires minimal operator involvement with no mechanical pipetting. The system comprises (1) a whole blood sample disc, (2) a serum sample disc, (3) a sample preparation rotor, and (4) an analytical rotor. The blood sample disc and serum sample disc are designed with a plurality of precision bore capillary tubes arranged in a spoked array. Samples of blood are loaded into the blood sample disc in capillary tubes filled by capillary action and centrifugally discharged into cavities of the sample preparation rotor where separation of serum and solids is accomplished. The serum is loaded into the capillaries of the serum sample disc by capillary action and subsequently centrifugally expelled into cuvettes of the analytical rotor for analysis by conventional methods.

12 Claims, 3 Drawing Sheets

METHOD AND APPARATUS FOR AUTOMATED PROCESSING AND ALIQUOTING OF WHOLE BLOOD SAMPLES FOR ANALYSIS IN A CENTRIFUGAL FAST ANALYZER

BACKGROUND OF THE INVENTION

This invention was made in the course of a contract with the United States Department of Energy.

The invention relates generally to an extension and improvement of the utility of a centrifugal fast analyzer for blood serum analysis. More specifically, it relates to a capillary disc and rotor arrangement which prepares and simultaneously delivers each of a series of prepared and precisely measured serum sample aliquots to individual cuvettes in an analytical rotor.

Centrifugal fast analyzers (CFA), along with modifications and improvements, have been previously described in various disclosures and patents. See, for example, U.S. Pat. Nos. 3,555,284 and 3,798,459. A multiple-sample centrifugal rotor for blood fraction preparation has been described in U.S. Pat. No. 3,864,089. As taught therein, liquid or cell suspension products are removed by means of some type of withdrawal probe or pipet for analytical purposes. An improvement in that device is disclosed in U.S. Pat. No. 3,890,101 in which blood fractions are collected in removable containers or vials from which measured analytical samples are taken.

Ancillary equipment required for routine operation of these systems includes a sample and pipetting device, as described in U.S. Pat. No. 3,854,508, for loading aliquots of sample and reagents into chambers in the CFA rotor. Such loading devices are expensive, mechanically complicated and require considerable preventive maintenance. In clinical work, it would be of considerable advantage to eliminate the manual manipulations required of these devices by direct transfer of prepared, accurately measured blood serum samples to the cuvettes of an analytical rotor.

SUMMARY OF THE INVENTION

It is accordingly an object of the invention to provide a method and apparatus for preparing serum samples from whole blood.

It is another object of the invention to provide a method and apparatus, as above, in which precise aliquots of serum are loaded automatically into serum capillaries.

It is still another object of the invention to provide a method and apparatus, as above, which eliminates manual manipulations of serum samples during transfer to an analytical rotor.

It is yet another object of the invention to provide a method and apparatus, as above, which eliminates the need for ancillary equipment in serum sample preparation and transfer to an analytical rotor.

These objects and others are achieved by an apparatus for preparing blood samples for analysis, comprising a whole blood sample disc having a plurality of first radial passageways arranged therein in spoked array, each first passageway removably receiving a capillary tube for a whole blood sample; a serum sample disc secured to the whole blood sample disc and having a plurality of second radial passageways arranged therein in spoked array, each second passageway removably receiving a capillary tube; a sample preparation rotor having a center cavity for receiving and holding the whole blood and serum sample discs, the rotor including a plurality of separate cavities at the outer periphery thereof, the first and second radial passageways of the discs being oriented such that each of the whole blood sample capillary tubes is aligned with a single serum sample capillary tube to define a pair, each pair of capillary tubes being in fluid communication with a separate cavity; and means for rotating the sample preparation rotor to separate the whole blood samples into serum and solids in the separate cavities; wherein the serum migrates by capillary action from the cavities into the serum sample capillaries after rotation of the sample preparation rotor is halted.

The apparatus can further include an analytical rotor having a center cavity for removably receiving the serum sample disc and capillaries, and having a plurality of cuvettes and means for dispensing a measured amount of analytical reagent to each of the cuvettes; each of the serum sample capillaries being in fluid communication with a separate cuvette; and means for rotating the analytical rotor to effect transfer of the serum from the serum sample capillaries to the separate cuvettes for mixing with the dispensed analytical reagent.

The objects of the invention are further achieved by a method for preparing blood samples for analysis, comprising the steps of obtaining whole blood samples in a plurality of capillary tubes, placing each capillary tube in a separate radial passageway of a whole blood sample disc; placing the whole blood sample disc in a sample preparation rotor; disposing a serum sample disc above the whole blood sample disc, the serum sample disc having a plurality of empty serum capillary tubes received within radial passageways; aligning each empty capillary tube with a separate whole blood sample capillary tube to form a pair; aligning each pair of capillary tubes with a separate cavity along the periphery of the sample preparation rotor; rotating the sample preparation rotor to effect transfer of the whole blood samples from the capillaries to the cavities by means of the centrifugal force generated by rotation of the rotor; centrifugally separating the whole blood samples in the cavities into serum and solids by continued rotation of the rotor; stopping rotation and allowing the serum to migrate by capillary action into the serum capillary tubes; removing the serum sample disc from the sample preparation rotor and placing it in an analytical rotor containing a plurality of cuvettes and a means for dispensing analytical reagent into the cuvettes, each serum capillary tube being aligned with a separate cuvette and in fluid communication therewith; rotating the analytical rotor to effect transfer of the serum samples from the capillaries to the cuvettes by means of the centrifugal force generated by rotation of the rotor; transferring analytical reagent to each cuvette, the serum samples being mixed with the analytical reagent by continued rotation of the analytical rotor; and analyzing the serum samples.

DETAILED DESCRIPTION OF THE PREFERRED EMBODIMENTS

The present invention is a CFA-based disc and rotor system providing a means for processing measured whole blood samples into serum and solids (red cells and platelets), followed by aliquoting and transferring measured samples of the serum into the cuvettes of an analytical rotor. The system utilizes precision bore capillary tubes for volume measurement and comprises (1) a whole blood sample collection disc, (2) a sample preparation rotor, (3) a serum sample collection disc, and (4) an analytical rotor. The whole blood and serum sample collection discs are each equipped with a plurality of precision bore calibrated capillary tubes into which samples are loaded by capillary action. The samples are centrifugally discharged from the capillaries by high speed rotation of the rotors. Thus, a number of whole blood samples individually loaded into the capillaries of the whole blood sample disc are simultaneously transferred to cavities in the sample preparation rotor where they are centrifugally separated into serum and solids. The serum samples are individually and automatically loaded into empty capillaries of the serum sample disc by capillary action after the rotor is stopped. The filled serum capillaries are subsequently deposited into cuvettes of the analytical rotor, by centrifugation, for analysis by conventional photometric methods. This operation is accomplished withou the need for a special pipetting station such as that mentioned hereinbefore, or manual manipulation of the samples.

Figure 1:
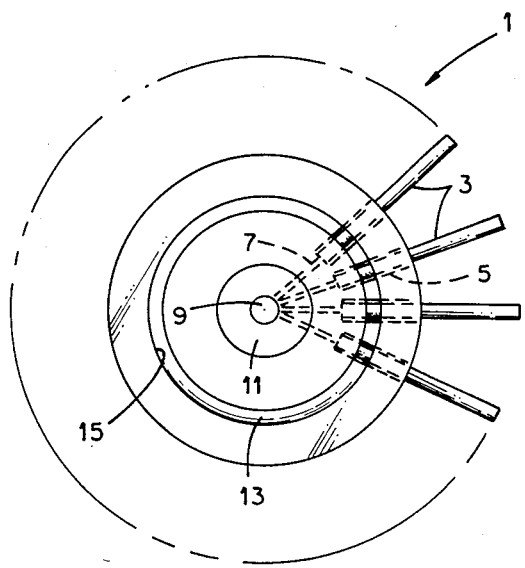
FIG. 1 is a top view of a whole blood sample disc constructed in accordance with this invention.

As shown in FIG. 1, a whole blood sample disc is indicated generally by the number 1. A plurality of precision bore capillary tubes 3 (four shown) are removably inserted into equally spaced radial passageways 5 arranged in spoked array in the disc 1. Each tube is atmospherically vented by way of a smaller passageway 7 connecting the radially inward end of the tube to an opening 9 through a raised, preferably circular center section 11 defining a hub. The tubes are held in place by suitable means such as an o-ring 13 positioned within a circular groove 15 that passes transversely across the tube-holding passageways. When the tubes are inserted, they are frictionally engaged by passing over and compressing the o-ring.

Figure 2:
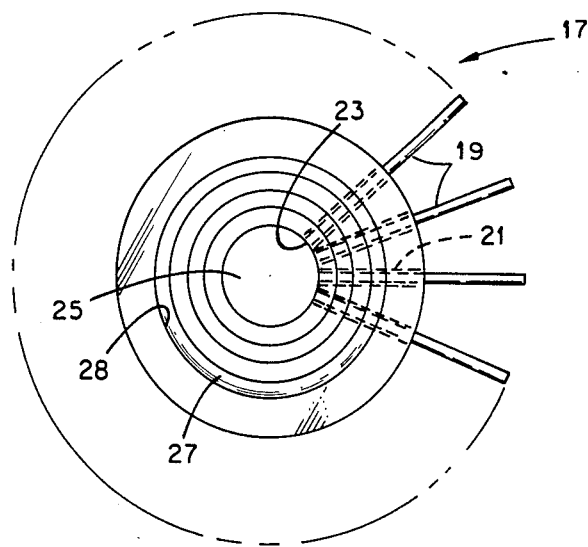
FIG. 2 is a top view of a serum sample disc.

Referring to FIG. 2, a serum sample disc, indicated generally by the number 17, comprises a plurality of precision bore capillary tubes 19 (four shown) removably inserted into equally spaced, radially arranged passageways 21 in disc 17. Each serum tube extends from the disc 17 in a spoked array and is atmospherically vented at the inner end by way of a vent groove 23 near the center opening 25. As in the whole blood sample disc, the tubes 19 are held in place by, for example, an o-ring 27 positioned within a circular groove 28 passing transversely across the tube-holding passageways 21. The o-ring is compressed as the tubes are inserted into the passageways. The center opening 25 in the center of the disc 17 accepts the raised circular section 11 at the center of the whole blood sample disc 1 to facilitate a precise mating of the two discs.

Figure 3:
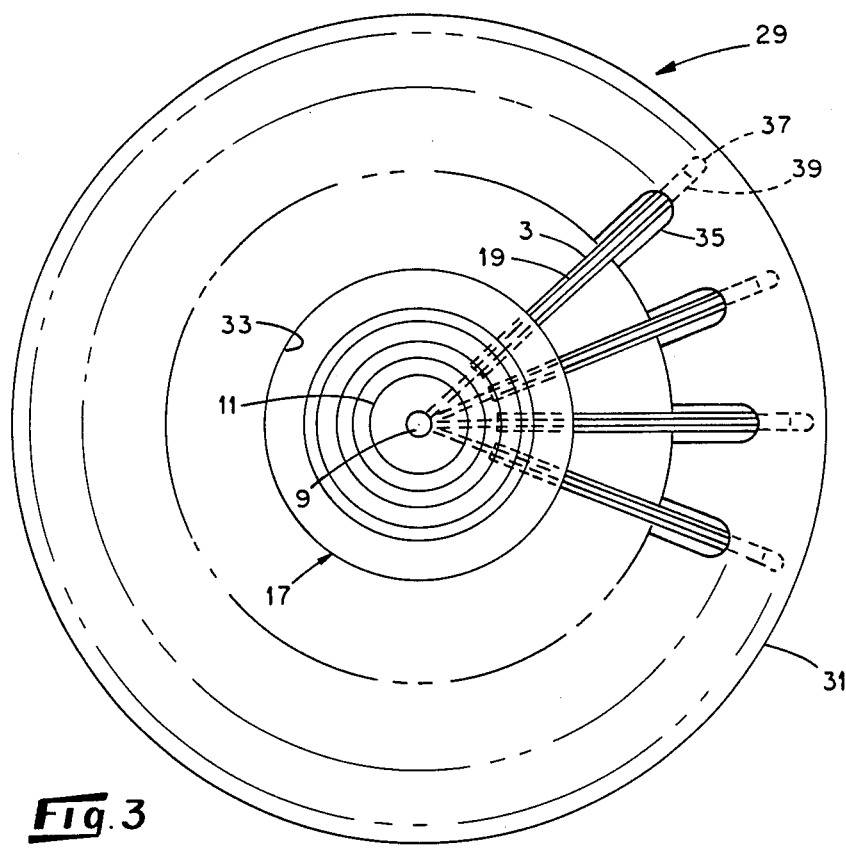
FIG. 3 is a top view of a sample preparation rotor.
Figure 4:
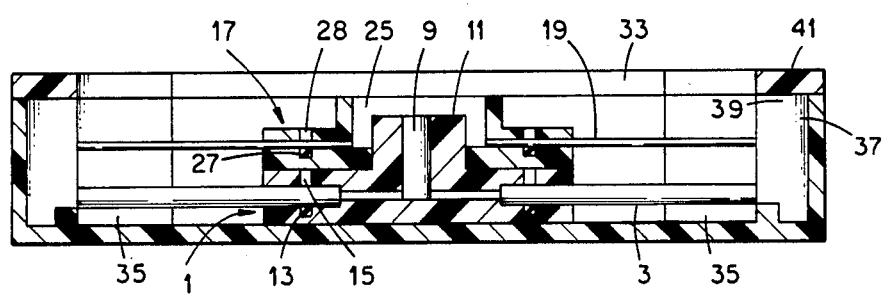
FIG. 4 is a cross-sectional elevation of the sample preparation rotor with blood sample disc and serum sample disc inserted.

A sample preparation rotor is shown in FIGS. 3 and 4 and is indicated generally by the number 29. The rotor 29 has a circular rotor body 31 with a center cavity 33 for receiving and holding the whole blood and serum sample discs. A multiplicity of radial slots 35 (four shown) are preferably provided in the outer raised portion of the rotor body to accommodate the capillaries 3 and 19 of the discs. The outer end of each slot communicates with a cavity 37 near the outer periphery of the rotor body by way of a passageway 39. The cavities and passageways are enclosed by a fixed top plate 41. Optionally, the top plate 41 can be configured to also cover the radial slots 35, the sample discs 1 and 17, or portions thereof.

As shown in FIG. 4, the whole blood sample disc 1, with capillaries 3 in place, is inserted into the hollow center 33 of the rotor, with each capillary 3 extending into a slot of the raised portion of the outer rotor body. The outer end of each capillary tube 3 is in direct communication with a passageway 39 leading to a cavity 37. The serum sample disc 17 with capillary tubes 19 in place is positioned directly above and mated to the whole blood sample disc by means of the center section 11 of the whole blood sample disc. As with the whole blood capillary tubes 3, the outer end of each capillary tube 19 is in direct communication with a separate passageway 39 leading to a cavity 37 at the outer periphery of the rotor body. The radial slots 35 ensure that each of the capillary tubes 3 are aligned with a capillary tube 19, each pair of tubes aligned with one of the passageways 39 and cavities 37. Alternative means for alignment can be provided, in which case the radial slots 35 can be eliminated.

Upon securement of both discs in the sample preparation rotor 29, the latter is rotated. Through centrifugal force the samples in the whole blood capillaries are drawn to the separate passageways 39 and into the cavities 37. The generated centrifugal force produces separation of the blood into serum and blood solids in the known manner, the solids in each blood sample migrating to the outermost peripheral portion of each cavity 37, resulting in a layer. The serum collects radially inward in the cavity. Upon effecting the desired separation, the rotor 29 is stopped with the top layers of serum being in contact with the capillary tubes 19 of the serum sample disc, and accordingly are drawn into the tubes by capillary action. The serum sample disc, complete with filled serum tubes, is then transferred to an analytical rotor.

Figure 5:
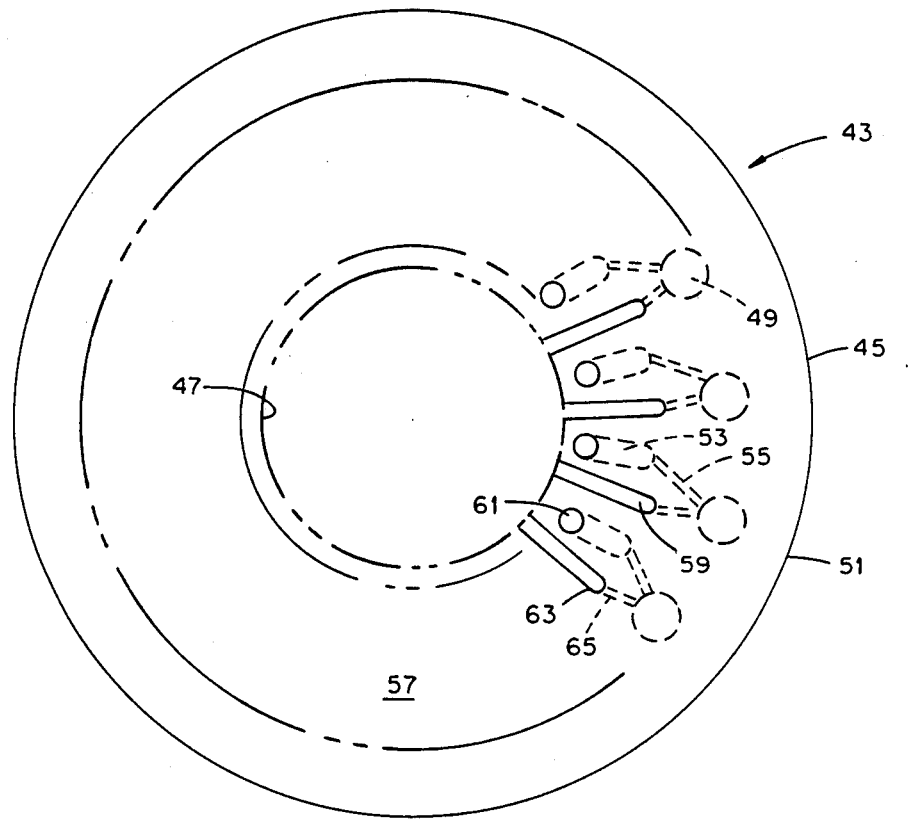
FIG. 5 is a top view of an analytical rotor.

An analytical rotor is shown in FIG. 5, and is indicated generally by the number 43. A circular rotor body 45 is fixed to a bottom cover (not shown). The rotor body is designed with a circular opening 47 at the center to accommodate the serum sample disc 17 (not shown). The rotor body 45 contains a plurality of equally spaced sample cuvettes 49 (four shown) located around the outer periphery 51 of the body. A cavity 53 for analyical reagents is located radially inward from each cuvette 49 and communicates with the cuvette by way of a small passageway 55. The cuvettes, cavities and reagent passageways are enclosed by a fixed top cover 57. A plurality of radial slots 59 are provided in the top cover and rotor body to accommodate the capillary tubes 19 (not shown) of the serum sample disc 17 (not shown). An opening 61 through the top cover is provided at each reagent cavity for filling of the reagent cavities 53. The outer terminus 63 of each slot 59 communicates with a separate cuvette 49 by way of a connecting passageway 65 in the rotor body.

In an alternative embodiment, reagent can be dispensed to the cuvettes via dynamic loading from a central location in the analytical rotor, rather than from individual reagent cavities. In dynamic loading, reagent is dispensed to the rotor while it is spinning and is distributed to each cuvette by centrifugal force. Generally, dynamic loading can be employed when only a single reagent is used for performing the same analysis on all the samples in the cuvettes. Where different analyses using different reagents on the samples are performed, static loading using separate reagent cavities as described above is preferred.

The analytical rotor is rotated at sufficient speed to cause the serum samples to be transferred by centrifugal force from the capillaries 19 through the connecting passageways 65 and into the cuvettes 49. Simultaneously, reagent from the reagent cavities 53 enters the cuvettes via passageways 55 and mixes with the samples. The cuvettes containing the individual samples and reagent can then be analyzed by conventional means.

The rotational speed required to produce the necessary centrifugal force in the sample preparation and analytical rotors is in part dependent on the diameter of the rotors, and those skilled in the art can readily ascertain the correct rotational speed for a given rotor diameter. Generally, rotational speeds can be varied from about 1000 to about 4000 rpm. Rotor diameters can vary upwards from a few centimeters. In a preferred embodiment, the rotors are about 8.7 cm in diameter. The capillary tubes can also vary in size depending on the rotor diameter. Whole blood capillaries of about 1 inch in length and with a capacity of from about 100 $\mu$l to about 200 $\mu$l are preferred. Serum capillaries are generally of a smaller diameter than whole blood capillaries. For example, a 1.000±0.002-in. length of precision bore tubing having an internal diameter of 0.0279±0.0005 in. can be used and will contain a volume of 10.0±0.4 $\mu$l of liquid. By using tubes of different internal diameters, various volumes of liquid may be obtained. Thus, the appropriate volume of serum sample required by a specific chemical assay may be obtained by selection and use of a 1-in. length of capillary of the appropriate internal diameter.

The invention is illustrated by the following example:

A whole blood sample (~200 $\mu$l) was loaded by capillary action into each capillary of a whole blood sample disc. Sample identification was accomplished by omitting one capillary tube from the disc to form a blank site, and numbering the remaining tubes in numerical order beginning with No. 2. The experimental system contained 16 active sample sites. A loaded whole blood sample disc was positioned in the sample preparation rotor with the blank site thereof located at a blank site in the rotor, and with each loaded capillary tube located in a rotor slot in communication with a passageway leading to a sample cavity in the rotor. The empty serum sample disc with one capillary tube omitted was positioned on top of the sample preparation rotor. Using the blank sites as a guide, the serum sample disc was placed in the rotor resting on and mated with the whole blood sample disc with the outer ends of the empty capillary tubes in contact with the inner openings of the passageways leading to the sample cavities in the rotor. The rotor, with two discs in place, was then rotated at high speed (~4000 rpm), the centrifugal force moving the whole blood sample from each capillary tube of the whole blood sample disc to the corresponding sample cavity in the rotor. High speed rotation was continued until the serum separated from the solids (red cells, platelets, etc.). The solids were contained in the outer portion of the cavity while the serum occupied the inner portion of the cavity and the passageway. The roor was then stopped and the serum from each active site on the rotor filled the corresponding capillary tube of the serum sample disc by capillary action. Thus, a known volume of serum from each blood sample was contained in a capillary tube of serum sample disc. Volumes of blood and serum samples could be varied by the use of capillary tubes with differing bore diameters.

The loaded serum sample disc was removed from the sample preparation rotor and placed in an analytical rotor which had the prescribed analytical reagents in the reagent cavities. The vacant site on the serum sample disc was situated in accord with a vacant site on the analytical rotor, and each loaded capillary tube was positioned into its respective slot with the outer end in direct communication with the passageway leading to a sample cuvette. The rotor was then rotated at 4000 rpm. The serum samples were moved by the centrifugal force from the capillary tubes through the passageways into the sample cuvettes. Simultaneously, the analytical reagents were moved from the reagent cavities through the connecting passageways to the sample cuvettes, where they mixed and reacted with the serum samples in preparation for analysis by conventional photometric methods.

The invention can be used in clinical laboratory blood analysis to extend and improve the capability of the some 40,000 centrifugal fast analyzers now in use. This system also has a potential for use in a zero-gravity environment. In addition, the system can be incorporated into a low-cost analytical system suitable for use in doctors' offices and other areas where high performance, economy and ease of operation are required.

The foregoing description of preferred embodiments has been set forth merely to illustrate the invention and is not intended to be limiting. Since modifications of the described embodiments incorporating the spirit and substance of the invention may occur to persons skilled in the art, the scope of the invention should be limited solely with respect to the appended claims and equivalents.

What is claimed is:

1. A system for preparing blood samples for analysis, comprising:

a whole blood sample disc having a plurality of first radial passageways arranged therein in spoked array, each said first passageway removably receiving a capillary tube for a whole blood sample;

a serum sample disc removably secured to said whole blood sample disc and having a plurality of second radial passageways arranged therein in spoked array, each said second passageway removably receiving a capillary tube;

a sample preparation rotor having a center cavity for receiving and removably holding said whole blood and said serum sample discs, where the serum sample and whole blood sample discs are rotatable with the rotor, said whole blood sample disc being positioned on said rotor below said serum sample disc, said rotor including a plurality of separate cavities at its outer periphery, said first and said second radial passageways of said whole blood and said serum sample discs being oriented such that a separate whole blood sample capillary tube is aligned with a separate serum sample capillary tube to define a pair, each said pair of capillary tubes being in fluid communication with one of said separate cavities; and means for rotating said sample preparation rotor to separate a plurality of whole blood samples into serum and solids in said separate cavities;

wherein said cavities and said serum capillary tubes are of sufficient size such that said serum migrates by capillary action from said separate cavities into said serum sample capillaries after rotation of the apparatus is halted.

2. A system as claimed in claim 1, wherein each pair of capillary tubes communicates with one of said separate cavities by means of a radial slot in said rotor, each of said radial slots positioned radially inward from, and communicating with, a separate cavity.

3. A system as claimed in claim 1, wherein the serum sample disc is secured on top of the whole blood sample disc by means of a raised circular section in the whole blood sample disc which mates with an opening at the center of the serum sample disc.

4. A system as claimed in claim 1, wherein the sample preparation rotor includes a fixed top plate for enclosing the cavities and passageways.

5. A system as claimed in claim 1, said system further including:

an analytical rotor having a center cavity for removably receiving said serum sample disc and serum sample capillaries, and having a plurality of cuvettes and means for dispensing a measured amount of analytical reagent to each of said cuvettes, each of said serum sample capillaries being in fluid communication with a separate cuvette; and means for rotating said analytical rotor to effect transfer of the serum from said serum sample capillaries to said separate cuvettes for mixing with said dispensed analytical reagent.

6. A system as claimed in claim 5, wherein the whole blood sample disc and the serum sample disc each include means for atmospherically venting the whole blood and serum sample capillaries.

7. A system as claimed in claim 1, wherein the whole blood and the serum capillary tubes are held in place in their respective discs by means of o-rings.

8. A system as claimed in claim 7, wherein each o-ring is located at the bottom of a circular groove in each disc, each circular groove passing transversely across the respective radial passageways.

9. A system as claimed in claim 5, wherein the means for dispensing analytical reagent comprises a plurality of reagent cavities, each said reagent cavity in fluid communication with one of said separate cuvettes, the reagent being transferred to each said cuvette during rotation of the analytical rotor.

10. A system as claimed in claim 9, wherein the analytical rotor includes a fixed top cover containing a plurality of radial slots for accommodating the serum capillary tubes.

11. A system as claimed in claim 10, wherein the fixed top cover of the analytical rotor further includes a plurality of openings passing through the cover, each opening communicating with one of said plurality of reagent cavities.

12. A method for preparing blood samples for analysis, comprising the steps of:

obtaining whole blood samples in a plurality of capillary tubes;

placing each capillary tube in a separate radial passageway of a whole blood sample disc;

placing the whole blood sample disc in a sample preparation rotor;

disposing a serum sample disc above the whole blood sample disc, the serum sample disc having a plurality of empty serum capillary tubes received within radial passageways;

aligning each empty serum capillary tube with a separate whole blood sample capillary tube to form a pair;

aligning each pair of capillary tubes with a separate cavity along the periphery of the sample preparation rotor;

rotating the sample preparation rotor to effect transfer of the whole blood samples from the capillaries to the cavities by means of the centrifugal force generated by rotation of the rotor;

centrifugally separating the whole blood samples in the cavities into serum and solids by continued rotation of the rotor;

stopping rotation and allowing the serum to migrate by capillary action into the serum capillary tubes;

removing the serum sample disc from the sample preparation rotor and placing it in an analytical rotor, said analytical rotor containing a plurality of cuvettes and a means for dispensing analytical reagent into said cuvettes, each serum capillary tube aligned with a separate cuvette and in fluid communication therewith;

rotating the analytical rotor to effect transfer of the serum samples from the capillaries to the cuvettes by means of the centrifugal force generated by rotation of the rotor;

transferring analytical reagent to each cuvette, the serum samples being mixed with the analytical reagent by continued rotation of the analytical rotor; and analyzing the serum samples.

* * * * *